United States Patent [19]

O'Brien et al.

[11] Patent Number: 5,747,272
[45] Date of Patent: May 5, 1998

[54] **DETECTION OF SHIGA-LIKE TOXINS OF ENTEROHEMORAGIC *ESCHERICHIA COLI***

[75] Inventors: Alison O'Brien, Bethesda, Md.; Susanne Ward Lindgren, Portland, Oreg.; Liyanage Parakrama Perera, Rockville, Md.; Nancy A. Strockbine, Lithonia, Ga.; Angela Ruth Melton-Celsa, Sterling, Va.

[73] Assignee: Henry M. Jackson Foundation for the Advancement of Military Medicine, Rockville, Md.

[21] Appl. No.: 412,231

[22] Filed: Mar. 10, 1995

Related U.S. Application Data

[63] Continuation of Ser. No. 195,066, Feb. 14, 1994, abandoned.
[51] Int. Cl.[6] .................. G01N 33/569; G01N 33/53
[52] U.S. Cl. ............... 435/7.37; 435/7.32; 435/7.92; 435/7.95; 435/975; 435/968; 530/388.4; 530/389.5
[58] Field of Search ................. 435/7.37, 7.32, 435/7.92, 7.95, 975, 968; 530/388.4, 389.5

[56] References Cited

U.S. PATENT DOCUMENTS 4,598,044  7/1986  Kricka et al. ........................ 435/28

OTHER PUBLICATIONS

Perera et al, *J. Clin. Microbiol.*, vol. 26, No. 10, pp. 2127–2131, Oct. 1988.

American Type Culture Collection Catalogue of Cell Lines & Hybridomas. 7th Ed. 1992.

Strockbine et al., *Infection and Immunity*, vol. 50, No. 3, pp. 695–700, Dec. 1985.

Amersham, Life Science Products Catalog, 1992.

*Primary Examiner*—Toni R. Scheiner
*Attorney, Agent, or Firm*—Finnegan, Henderson, Farabow, Garrett and Dunner, L.L.P.

[57] ABSTRACT

A rapid, sensitive, non-radioactive diagnostic kit for the direct detection of both Shiga-like toxin, type I, and Shiga-like toxin, type II, produced by enterohemorrhagic *Escherichia Coli* in food and clinical samples. This diagnostic kit is comprised of a monoclonal antibody capable of detecting Shiga-like toxin, type I, and a monoclonal antibody capable of detecting Shiga-like toxin, type II, together with a chemiluminescing detection reagent with a sensitivity enhancer.

25 Claims, No Drawings

DETECTION OF SHIGA-LIKE TOXINS OF ENTEROHEMORAGIC *ESCHERICHIA COLI*

This is a continuation, division, of application Ser. No. 08/195,066, filed Feb. 14, 1994, now abandoned.

STATEMENT OF GOVERNMENT INTEREST

The invention described herein may be manufactured, used and licensed by or for the Government for governmental purposes without payment to us of any royalties thereon.

BACKGROUND OF THE INVENTION

This invention generally relates to the detection of Shiga-like toxins by means of a fast, highly sensitive assay without necessity of tissue culture. As such, the invention presents a novel means of testing for the presence of toxins in food products and clinical stool samples, and may be used to quantify the amount of toxin occurring in the sample.

Infection with Enterohemorrhagic *Escherichia coli* (EHEC) is associated with food-borne outbreaks of diarrhea, hemorrhagic colitis and the hemolytic uremic syndrome. Hemorrhagic colitis is characterized by severe abdominal pain with watery diarrhea. This is followed by grossly bloody diarrhea without fever (Riley, L. W., 1987, The epidemiologic, clinical, and microbiological features of hemorrhagic colitis, Ann. Rev. of Microbiology 41:383–407). The symptoms typically last from four to eight days. The illness is usually self-limiting. Hemolytic uremic syndrome associated with EHEC is characterized by a thrombocytopenia, microangiopathic hemolytic anemia and acute renal failure (Levin, et al., 1989, Hemolytic uremic syndrome, Adv. Pediatric Infectious Disease 4:51–82). The illness occurs predominantly in children under four years of age.

EHEC infections are predominantly associated with industrialized and developing countries. Reports of EHEC infections have suggested transmission through a variety of food products of animal origin, including meat, poultry, and animal products such as unpasteurized milk. The transmission of EHEC may also be accomplished by person to person contact and has been reported as the source of outbreaks at day care centers (Spika, et al., 1986, Hemolytic-uremic syndrome associated with *Escherichia coli* 0157:H7 in a day care center, J. Pediatr. 109:287–291; Belongia, et al., 1993, Transmission of *Escherichia coli* 0157:H7 infection in Minnesota child day-care facilities, JAMA 269:883–888).

EHEC infections are particularly associated with the developed and developing countries where significant amounts of beef are consumed. In particular, EHEC is associated with consumption of undercooked hamburger meat. One such instance involved an outbreak in February 1993 in the western United States apparently originating with consumption of hamburger at a chain of fast food restaurants (Centers for Disease Control, 1993, "Update: Multistate outbreak of *Escherichia Coli* 0157:H7 infections from hamburgers—Western United States," MMWR Vol. 42, pp. 258–263).

A common characteristic of EHEC strains is the production of Shiga-like toxins (SLTs), also known as Vero toxins. Shiga-like toxins are multiple subunit toxins, consisting of one enzymatically active A subunit and five receptor-binding B subunits. Shiga-like toxins have been categorized in two groups based on binding property and immunological activity.

The first group, designated Shiga-like toxin type I (SLT-I), includes the prototype toxin SLT-I and Shiga toxin from *Shigella disenteriae* type I. Shiga toxin and SLT-I differ by only one amino acid and are considered to be the same toxin. No other homologous toxins are currently known to exist. Both SLT-I and Shiga toxin use the glycolipid globotriaosylceramide (Gb$_3$, Gal$\alpha$1-4Gal$\beta$1-4Glc$\beta$1-1Cer) as the functional eucaryotic cell-surface receptor. Hereinafter, the designation Shiga-like toxin type I or SLT-I will be understood to include Shiga toxin produced by *Shigella disenteriae* type I. SLT-I can be neutralized by antiserum to purified Shiga toxin and by monoclonal antibodies to the B subunit to of SLT-I.

The second group, Shiga-like toxin type II, cannot be neutralized by anti-SLT-I monoclonal or polyclonal antisera. This group exhibits sequence and antigenic variation. The prototype SLT-II toxin is produced by EHEC 0157:H7. The prototype toxin shares 55 and 57 percent deduced amino acid sequence homology with SLT-I A and B subunits respectively. Another member of the group, SLT-IIv, is responsible for edema disease in swine. SLT-IIv demonstrates 93 and 84 percent deduced amino acid sequence homology with the prototype SLT-II A and B subunits respectively. SLT-IIv more avidly binds globotetraosylceramide (Gb$_4$, GalNAc$\beta$1-3Gal$\alpha$1-4Gal$\beta$1-4Glc$\beta$1-1Cer), whereas the other SLT-II toxins, like their SLT-I counterparts, use Gb$_3$ as the cell surface receptor.

Since 1990, additional Shiga-like toxins have been described which are considered members of the SLT-II group. This classification is based on their sequence homology and immunological cross-reactivity with SLT-II. The additional members include SLT-IIvha, SLT-IIvhb and SLT-IIc. Those members which have been amino acid sequenced are nearly 97 percent homologous to the prototype SLT-II strain in both the A and B subunits.

The potential for extensive outbreaks of enterohemorrhagic colitis resulting from contaminated food has produced the need for a fast, simple and sensitive test for detection of all SLTs. To be effective, any such test must be capable of detecting the presence of all Shiga-like toxins. Existing tests capable of detecting SLTs have failed to provide the necessary rapidity, the requisite specificity or both.

One assay is specific for detecting SLT-II produced by *E. Coli* 0157:H7 (Doyle, et al., 1987, "Isolation of Escherichia Coli 0157:H7 from Retail Fresh Meats and Poultry," Applied and Environmental Microbiology, 53:2394–2396). This method requires incubating a sample in an enrichment medium overnight. The sample is then filtered through hydrophobic grid membrane paper. The filter paper is then placed on a nitrocellulose paper and the nitrocellulose paper is again incubated overnight with an enrichment medium. The toxins are then detected using an antibody to the toxin and standard immunoblot procedures. The procedure is time consuming and complex. Furthermore, the procedure does not detect all SLTs.

Other assays are available for detection of EHEC, particularly *E. Coli* 0157:H7. These assays detect the presence of the organism rather than the toxin it produces. One such assay is described in U.S. Pat. No. 5,168,063. The antibody described in that patent reacts with a protein in the outer membrane of the EHEC having molecular weight of approximately 13,000 daltons. The patent also describes a method of using the antibody in an assay for detecting the presence of the EHEC. The assay, however, requires the incubation of the sample believed to contain EHEC, which is time-consuming and requires that the user have adequate tissue culture facilities.

Further, previously known assays for EHEC and their toxins have generally relied on radiolabeling as a detection means because radiolabeling offered the requisite degree of sensitivity. Radiolabeling has several disadvantages, however. Radiolabeling involves the use of hazardous agents, requiring the protection of the user and the safe disposal of the waste. Radiolabeling is also time consuming to conduct.

SUMMARY OF THE INVENTION

It is an object of the present invention to provide a means for detecting both Shiga-like toxins, type I (SLT-I) and type II (SLT-II) in a single assay. It is also an object of the invention to provide a means for detecting the presence of substantially all enterohemorrhagic E. Coli which produce SLTs by means of a single assay directed against the product toxins.

It is further an object of this invention to provide a means for rapidly detecting the presence of SLT-producing EHEC in clinical samples, such as stool samples. It is also an object of the invention to provide a means for rapidly detecting the presence of SLTs and SLT-producing EHEC in food samples.

It is further an object of this invention to provide a means for detecting SLTs in food and clinical samples which is highly sensitive and relatively safe for the user. It is also an object of this invention to provide a means for detecting SLTs which does not involve tissue culture.

It is further an object of this invention to provide diagnostic kits for assaying the presence of both SLT-I and SLT-II in food or other samples. It is an object of this invention to provide diagnostic kits capable quantifying the level of toxin found in a clinical or food sample.

This invention is a diagnostic kit for detecting the presence of SLT-I and SLT-II, specifically in food and clinical samples. The kit is comprised of two heterologous monoclonal antibodies in an aqueous solution and a sensitive chemiluminescent detection reagent. One of the antibodies is produced from a hybridoma formed by the fusion of a mouse myeloma line and spleen cells from mice immunized with SLT-I and selected for its specificity for the SLT-I B subunit. The other antibody is produced from a hybridoma formed by the fusion of a mouse myeloma line and spleen cells immunized with a toxoid derived from SLT-II and selected for its specificity for the SLT-II A subunit. The chemiluminescent detection reagent is a solution of a chemiluminescing compound, an oxidant and a sensitivity enhancer. In the presence of a peroxidase enzyme which is conjugated either to a secondary antibody or directly to the previously described monoclonal antibodies, the chemiluminescing compound is oxidized to an excited state, which emits a measurable amount of light when returning to a non-excited state. In order to produce the requisite sensitivity for the detection of low to moderate amounts of SLT, a sensitivity enhancer is included in the detection reagent.

DETAILED DESCRIPTION OF THE INVENTION

The methods for preparing monoclonal antibodies generally are well known to those in the art. In preparation of monoclonal antibodies against SLT-I, BALB/c mice are immunized with biologically active Shiga toxin from *Shigella dysenteriae*, type 1, or SLT from an SLT-I producing *E. Coli*, such as strain H30, using methods well-known in the art. The mice are sacrificed and their splenocytes are harvested. The splenocytes are fused to an appropriate mouse myeloma cell line according to methods well-known in the art. The hybridomas are then cultured and the cell culture supernatants are screened for toxin-specific antibodies. Hybridomas positive for antibody activity are selected and expanded. Perpetual cell lines can then be maintained according methods well-known in the art.

A monoclonal antibody-producing hybridoma was generated in this manner by Strockbine, et al., from the fusion of SP2/0-Ag14 myeloma cells and BALB/c mice immunized with purified, biologically active SLT from *E. coli* H30. This hybridoma was designated 13C4 (Strockbine, N. A., Marques, L. R. M., Holmes, R. K, and O'Brien, A. D., 1985, Characterization of Monoclonal Antibodies against Shiga-Like Toxin from *Escherichia coli*, Infection and Immunity, 50:695–700). This antibody is generally characterized as being of the G1 heavy and kappa light chain classes. This hybridoma was deposited at the American Type Culture Collection, 12301 Parklawn Drive, Rockville, Md. 20852, USA and was assigned catalogue number CRL 1794. This hybridoma is hereinafter referenced as ATCC CRL 1794.

The monoclonal antibodies against SLT-II are prepared from a toxoid derived from SLT-II toxin. Crude SLT-II toxin is produced from toxin-converting phage plaque preparations by means of coliphage plaque lawns using techniques known in the art. The crude toxin is then converted to toxoid by treatment with formaldehyde or glutaraldehyde in $Na_2HPO_4$ and the remaining formaldehyde or glutaraldehyde is removed.

Female BALB/c mice are immunized with the toxoid. The mice are then sacrificed and their splenocytes are harvested. The spleen cells are prepared and fused to Sp2/0-Ag 14 mouse myeloma cells by methods well-known in the art. The resulting hybridomas are then cultured. The culture supernatants are assayed and those cultures showing positive for antibody activity are selected and expanded. Perpetual cell lines can then be maintained using methods well-known in the art.

Two monoclonal antibody-producing hybridomas were generated in this manner by Perera, et al., from the fusion of SP2/0-Agl4 myeloma cells and BALB/c mice immunized with formilinized SLT-II toxoid (Perera, L. P., Marques, L. R. M., and O'Brien, A. D., 1988, Isolation and Characterization of Monoclonal Antibodies to Shiga-Like Toxin II of Enterohemorrhagic *Escherichia coli* and Use of the Monoclonal Antibodies in a Colony Enzyme-Linked Immunosorbent Assay. J. Of Clinical Microbiology 26:2127–2131). One of the hybridomas, designated 11F11, is characterized as being of the IgM class, having a kappa light chain. The other hybridoma, designated 11E10, is characterized as being of the $IgG_1$ subclass with a kappa light chain. These hybridomas were deposited at the American Type Culture Collection, 12301 Parklawn Drive, Rockville, Md. 20852, USA. Hybridoma 11E10 was assigned catalogue number CRL 1907 and hybridoma 11F11 was assigned catalogue number CRL 1908. Hereinafter these hybridomas will be referenced as ATCC CRL 1907 and ATCC CRL 1908, respectively. Both ATCC CRL 1907 and ATCC CRL 1908 react with the A subunit of SLT-II but not with the B subunit.

Bacterial culture samples are spotted onto a nitrocellulose membrane preferably using a dot blot apparatus connected to a vacuum. The membrane is air dried and then incubated in a solution containing a biological detergent and a blocking agent capable of blocking nonspecific binding sites. The solution such as phosphate buffered saline with 0.1% Tween 20 (PBS-T) and 5% non-fat dry milk may be used. After an appropriate period of incubation the membrane is washed to remove excess blocking agent.

The membrane is next incubated in a mixture of two monoclonal antibodies (one specific for the SLT-I and the other specific for SLT-II) diluted in PBS-T to allow the antibodies to bind to any SLTs which may be present in the culture samples. The monoclonal antibody against SLT-I may be any monoclonal antibody which is specific for SLT-I, but generally will be specific for the B subunit of SLT-I. Similarly, the monoclonal antibody against SLT-II may be any monoclonal antibody which are specific for SLT-II, but generally will be specific for the A subunit of SLT-II. In the preferred embodiment, the monoclonal antibodies specific for SLT-I are the antibodies produced by the hybridoma ATCC CRL 1794 and the monoclonal antibodies specific for SLT-II is the antibodies produced by hybridoma ATCC CRL 1907. Dilutions of ATCC CRL 1794, ATCC CRL 1907 and ATCC CRL 1908 in phosphate buffered saline ranging from 1:2 to 1:64 are sufficiently sensitive for the purposes described herein.

After appropriate incubation, the monoclonal antibody mixture is removed and the membrane is washed to remove any remaining monoclonal antibodies which have not bound to the samples. The samples are then assayed for the presence of bound antibodies using western blotting techniques and an enhanced chemiluminescent compound.

The membrane is incubated in a solution containing a secondary antibody which has been conjugated to a peroxidase enzyme as a label. The secondary antibody is allowed to bind to any anti-SLT antibody present on the membrane. The sample is then washed to remove unbound secondary antibody. The membrane is immersed in a detection reagent consisting of a chemiluminescent compound, an oxidant and a compound capable of enhancing the luminescing reaction which occurs with peroxidase-catalyzed oxidation of the oxidant in the presence of the chemiluminescent compound. The amount of bound antibody is measured by detecting the luminescence of the sample.

Western blotting techniques using a chemiluminescent label are preferred as a rapid, highly sensitive and non-radioactive assay. After exposure to the antibody of the invention, the membrane is incubated in a horseradish peroxidase-conjugated anti-mouse immunoglobulin G antibody and then washed to remove any unbound antibody. The membrane is then immersed in a detection reagent containing an oxidant, a chemiluminescing compound and a phenolic enhancer.

The chemiluminescent reaction is a peroxidase-catalyzed reaction of an oxidant and a chemiluminescent compound. In ELISAs, the peroxidase enzyme is conventionally a horseradish peroxidase enzyme which has been conjugated to an anti-mouse immunoglobulin antibody. However, other peroxidases, particularly plant peroxidases, may be substituted. Where each of the heterologous monoclonal antibodies are diluted in the range of 1:2 to 1:64, a horseradish peroxidase-conjugated goat antimouse immunoglobulin G antibody may be used in a dilution with a physiological buffered saline solution in the range of 1:500 to 1:5000.

Chemiluminescent compounds provide a rapid and safe means for conducting immunoassays. Chemiluminescent compounds are converted to an excited state during the oxidation reaction and return to a non-excited state through the emission of light. Chemiluminescent compounds are generally described as being 2,3-dihydro-1,4-phthalazinedione (DPD) compounds capable of emitting light through the previously described oxidation reaction. The most commonly used DPD compounds are luminol (5-amino-2,3-dihydro-1,4-phthalazinedione) and isoluminol (6-amino-2,3-dihydro1,4-phthalazinedione).

Solutions containing chemiluminescent DPD compounds, alone, are not sufficiently sensitive to detect low, but clinically significant, amounts of SLT in samples. The sensitivity of chemiluminescent reaction is therefore enhanced by the addition of a phenol or naphthol having a general formula as described in U.S. Pat. No. 4,598,044 at column 2, line 37 through column 3, line 3 and column 4, lines 28–45. The described phenols and naphthols capable of enhancing the sensitivity of the chemiluminescing reaction are hereinafter referred to as sensitivity enhancers.

The oxidant will be selected for its ability react with the predetermined DPD compound, resulting in the emission of light. Commonly used oxidants include hydrogen peroxide and solutions containing perborate ion.

After immersion, the membrane is immediately exposed to a photographic film capable of detecting the light emitted from the peroxidase catalyzed reaction of the detection reagent. The exposure time is dependant upon the film used but generally will range from approximately 10 second to 3 minutes. The presence of toxin can then be detected when the film is exposed.

Physiologically buffered saline solutions, biological detergents and blocking agents capable of blocking nonspecific binding sites are all well known to the art and practitioners will readily appreciate that a wide range of combinations could be substituted for preferred solution without significantly affecting the sensitivity of the assay. For example, bovine serum albumen (BSA) may be substituted for nonfat dry milk as a blocking agent. Similarly, borate, carbonate, acetate, and Tris [tris(hydromethyl) aminomethane] could be substituted for phosphate as a buffer. Further, any biological detergent generally having similar properties to Tween-20 may be substituted. The chemiluminescent reaction will generally occur over a range of pH from 6 to 10, but preferably would be within a range of pH 7–9.

Enzyme-linked Immunosorbent Assays (ELISAs) are generally-known means of assaying for the presence of antigens in test material. Those familiar with art will readily appreciate that invention described herein may be adapted to other conventional ELISA techniques. For example, the peroxidase enzyme may be conjugated directly to the monoclonal antibodies against SLT-I and SLT-II. In such case, the use of an anti-mouse secondary antibody would be omitted.

Specifically, the invention is a diagnostic kit where the two heterologous monoclonal antibodies are used as a probe to carry out the method described above. Such kits would include antibodies against SLT-I and antibodies against SLT-II in aqueous solution, together with an enhanced chemiluminescent detection reagent containing a chemiluminescent DPD and a sensitivity enhancer, which is a phenol or naphthol capable of enhancing the sensitivity of the chemiluminescing reagent.

For a convenient, rapid test to determine the presence of any SLT, the two heterologous antibodies may be provided as a mixture in a single aqueous solution. In other embodiments, however, the kits may include two solutions, one containing only antibodies against SLT-I and the other containing antibodies only against SLT-II.

Conventionally, the kits would also include a substrate on which to perform the assay, wash solutions, a secondary antibody capable of binding the previously-described monoclonal antibodies and which is conjugated to a peroxidase enzyme, and film or other means for detection of the light produced by the chemilumenescent reaction, reagents necessary for processing the light detection means, and instructions for the use of the kit. In such conventional kit, the antibody mixtures and all reagents would be provided in standardized dilutions, such that the user would need only to prepare the sample, including serial dilution (if desired), and proceed with the assay according to the directions provided.

The chemiluminescent reaction will occur adequately at normal room temperatures. Accordingly, no special apparatus or facility will normally be required for temperature maintenance when using the kit.

Although the description and example of the invention provided herein demonstrate a simple kit for detection of SLT in food or clinical samples, those familiar with art will readily understand that other forms of the kit will allow the user to detect the relative quantity of toxin contained in a sample. By way of example, such a kit may use a means for measuring the amount of light emitted by the chemiluminescent assay of a clinical sample, or the kit may provide for the assay of a sample culture against one or more series of cultures having predetermined quantities of toxin.

WORKING EXAMPLE

Bacterial cultures are spotted onto BAS-NC™ nitrocellulose (Schleicher & Schuell, Inc., Keene New Hampshire) through a 96-well dot blot apparatus (Schleicher & Schuell, Inc.) connected to a vacuum. The nitrocellulose membrane is air-dried and incubated for 1 hour at room temperature in phosphate-buffered saline with 0.1% Tween 20 (PBS-T) (Bio-Rad Laboratories) containing 5% non-fat dry milk (Carnation Co., Los Angeles Calif.). The membrane is washed with PBS-T and then incubated with a mixture of monoclonal antibodies ATCC CRL 1794 [1:5 dilution] and ATCC CRL 1907 [1:5 dilution] in PBS-T for 1 hour. The membrane is washed three times with PBS-T to remove unbound antibody. The membrane is then incubated for 1 hour with a 1:500 dilution of horseradish peroxidase-conjugated goat anti-mouse immunoglobulin G antibody (Bio-Rad Laboratories) in PBS-T. After incubation, the membrane is washed five times in PBS-T, immersed in ECL™ Western blotting detection reagent (Amersham International PLC, Little Chalfont, United Kingdom) for 1 minute and then immediately exposed to X-OMKT™ film (Eastman Kodak Company, Rochester, N.Y.), for approximately 3 minutes, after which the film is developed and the presence of toxins detected.

We claim:

1. A diagnostic kit for the detection of Shiga-like toxins comprising
    an SLT antibody reagent comprising an antibody specific to Shiga-like toxin, type I, and an antibody specific to Shiga-like toxin, type II, in aqueous solution; and
    a detection reagent comprising a chemiluminescent 2,3-dihydro-1,4-phthalizinedione and a sensitivity enhancer capable of enhancing the sensitivity of the chemiluminescent 2,3dihydro-1,4-phthalizinedione reaction.

2. The diagnostic kit of claim 1, wherein the chemiluminescent 2,3-dihydro-1,4-phthalizinedione is selected from luminol or isoluminol, and the sensitivity enhancer is selected from 4-iodophenol, 4-phenylphenol or 2-chloro-4-phenylphenol.

3. The diagnostic kit of claim 1, having as an additional component a labelling reagent comprising a horseradish peroxidase labelled antibody directed against the antibodies of the SLT antibody reagent in an aqueous solution.

4. The diagnostic kit of claim 1, wherein the detection reagent is further comprised of hydrogen peroxide.

5. A diagnostic kit for the detection of Shiga-like toxins comprising
    an antibody specific to Shiga-like toxin, type I, in aqueous solution;
    an antibody specific to Shiga-like toxin, type II, in aqueous solution; and
    a detection reagent comprising a chemiluminescent 2,3-dihydro-1,4-phthalizinedione and a sensitivity enhancer capable of enhancing the sensitivity of the chemiluminescent 2,3-dihydro-1,4-phthalizinedione reaction.

6. The diagnostic kit of claim 5, wherein the chemiluminescent 2,3-dihydro-1,4-phthalizinedione is selected from luminol or isoluminol, and the sensitivity enhancer is selected from 4-iodophenol, 4-phenylphenol or 2-chloro-4-phenylphenol.

7. The diagnostic kit of claim 5, wherein the detection reagent is further comprised of hydrogen peroxide.

8. The diagnostic kit of claim 5, having as an additional component a labelling reagent comprised of a horseradish peroxidase labelled antibody directed against the antibody specific to Shiga-like toxin, type I, and the antibody specific to Shiga-like toxin, type II.

9. The diagnostic kit of claim 1 wherein the antibody specific to Shiga-like toxin, type I, is 13C4, produced by ATCC CRL 1794 and the antibody specific to Shiga-like toxin, Type II is 11E10 produced by ATCC CRL 1907.

10. The diagnostic kit of claim 1 wherein the antibody specific to Shiga-like toxin, type I is 13C4, produced by ATCC CRL 1794 and the antibody specific to shiga-like toxin, type II is 11F11 produced by ATCC CRL 1908.

11. The diagnostic kit of claim 5, wherein the antibody specific to Shiga-like toxin, type I is 13C4, produced by ATCC CRL 1794.

12. The diagnostic kit of claim 5, wherein the antibody specific to Shiga-like toxin, type II, is selected from 11F10, produced by ATCC CRL 1907 and 11F11, produced by ATCC CRL 1908.

13. The diagnostic kit of claim 5, wherein the antibody specific to Shiga-like toxin, type I, is 13C4, produced by ATCC CRL 1794 and the antibody specific to Shiga-like toxin, type II, is 11E10 produced by ATCC CRL 1907.

14. A diagnostic kit of claim 5, wherein the antibody specific to Shiga-like toxin, type I, is 13C4, produced by ATCC CRL 1794 and the antibody specific to Shiga-like toxin, type II is 11F11 produced by ATCC CRL 1908.

15. A method of qualitatively or quantitatively determining the presence or amount of substantially all Shiga-like toxins in a test sample which comprises, in the first step, contacting the test sample with a SLT antibody reagent comprising an antibody specific to Shiga-like toxin, type I and an antibody specific to Shiga-like toxin, type II, in aqueous solution; in a second step, contacting the product of the first step with a detection reagent; and in a third step, determining the specific binding of said SLT antibody reagent as a determination of the Shiga-like toxins in the test sample.

16. The method in accordance with claim 15 wherein the detection reagent comprises a chemiluminescent 2,3-dihydro-1,4phthalizinedione and a sensitivity enhancer capable of enhancing the sensitivity of the chemiluminescent 2,3-dihydro-1,4phthalizinedione reaction.

17. The method in accordance with claim 15 wherein the antibody specific to Shiga-like toxin, type I, is 13C4, produced by ATCC CRL 1794 and the antibody specific to Shiga-like toxin, type II, is 11E10 produced by ATCC CRL 1907.

18. The method in accordance with claim 15 wherein the antibody specific to Shiga-like toxin, type I, is 13C4, produced by ATCC CRL 1794 and the antibody specific to shiga-like toxin, type II, is 11E11 produced by ATCC CRL 1908.

19. The method in accordance with claim 15 wherein the chemiluminescent 2,3-dihydro-1,4-phthalizinedione is selected from luminol or isoluminol, and the sensitivity enhancer is selected from 4-iodophenol, 4-phenylphenol or 2-chloro-4phenylphenol.

20. The method in accordance with claim 15 having as an additional component a labelling reagent comprising of a horseradish peroxidase labelled antibody directed against the antibodies of the SLT antibody reagent in an aqueous solution.

21. The method in accordance with claim 15 wherein the detection reagent is further comprised of hydrogen peroxide.

22. A diagnostic kit for the detection of Shiga-like toxins comprising

An SLT antibody reagent comprising an antibody specific to Shiga-like toxin, type I, and an antibody specific to Shiga-like toxin, type II, in aqueous solution; and a detection reagent.

23. The diagnostic kit of claim 22 wherein the antibody specific to Shiga-like toxin, type I is 13C4, produced by ATCC CRL 1794.

24. The diagnostic kit of claim 22 wherein the antibody specific to Shiga-like toxin, type II, is 11E10, produced by ATCC CRL 1907.

25. The diagnostic kit of claim 23 wherein the antibody specific to Shiga-like toxin, type II, is 11F11, produced by ATCC CRL 1908.

* * * * *

UNITED STATES PATENT AND TRADEMARK OFFICE
CERTIFICATE OF CORRECTION

PATENT NO.   :   5,747,272

DATED        :   May 5, 1998

INVENTOR(S)  :   Alison O'Brien et al.

It is certified that error appears in the above-identified patent and that said Letters Patent is hereby corrected as shown below:

On the Title Page, Item [54], in the Title, line 2, "ENTEROHEMORAGIC" should read -- ENTEROHEMORRHAGIC --.
Column 1, line 2, "ENTEROHEMORAGIC" should read --ENTEROHEMORRHAGIC--.
In Claim 1, Col. 7, line 55, "2,3dihydro-1" should read --2,3-dihydro-1--.

In Claim 10, Col. 8, line 30, "shiga-like" should read -- Shiga-like --.

In Claim 16, Col. 8, line 60, "4 phthalizinedione" should read -- 4-phthalizinedione --.

In Claim 16, Col. 8, line 62, "4phthalizinedione" should read -- 4-phthalizinedione --.

In Claim 18, Col. 9, line 4, "shiga-like" should read -- Shiga-like --.

In Claim 19, Col. 9, line 10, "2-chloro-4phenylphenol" should read -- 2-chloro-4-phenylphenol --.

Signed and Sealed this

Twenty-eighth Day of July, 1998

*Attest:*

BRUCE LEHMAN

*Attesting Officer*    *Commissioner of Patents and Trademarks*